United States Patent
DuBois et al.

(10) Patent No.: US 7,373,939 B1
(45) Date of Patent: May 20, 2008

(54) TRACHEOTOMY PROCEDURE WITH INTEGRATED TOOL

(75) Inventors: Brian R. DuBois, Redwood City, CA (US); Luke W. Clauson, Redwood Shores, CA (US); Douglas T. Ellison, Plano, TX (US); Scott O. Chamness, Menlo Park, CA (US); Theodore M. Bender, Oakland, CA (US)

(73) Assignee: Cardica, Inc., Redwood City, CA (US)

( * ) Notice: Subject to any disclaimer, the term of this patent is extended or adjusted under 35 U.S.C. 154(b) by 180 days.

(21) Appl. No.: 11/367,904

(22) Filed: Mar. 3, 2006

(51) Int. Cl.
*A61M 11/00* (2006.01)

(52) U.S. Cl. ............................ 128/207.29; 128/200.26; 128/305.3

(58) Field of Classification Search .......... 128/207.29, 128/200.26, 305.3; 606/153, 151; 623/1.13
See application file for complete search history.

(56) References Cited

U.S. PATENT DOCUMENTS

| | | | |
|---|---|---|---|
| 3,643,649 A | 2/1972 | Amato | |
| 3,991,765 A | 11/1976 | Cohen | |
| 4,182,337 A | 1/1980 | Nickson | |
| 4,291,690 A | 9/1981 | Jessen | |
| 4,331,138 A | 5/1982 | Jessen | |
| 4,556,059 A | 12/1985 | Adamson, Jr. | |
| 5,048,518 A | 9/1991 | Eliachar et al. | |
| 5,681,323 A | 10/1997 | Arick | |
| 6,419,681 B1 | 7/2002 | Vargas et al. | |
| 6,428,550 B1 | 8/2002 | Vargas et al. | |
| 6,673,088 B1 | 1/2004 | Vargas et al. | |
| 2006/0135984 A1* | 6/2006 | Kramer et al. | 606/192 |

* cited by examiner

*Primary Examiner*—Steven O. Douglas
(74) *Attorney, Agent, or Firm*—Brian A. Schar

(57) ABSTRACT

An integrated tool may be used to perform a tracheotomy. The integrated tool may include a trocar and a delivery mechanism, where the delivery mechanism may deploy a stoma stent. The trocar may be actuated impulsively.

17 Claims, 7 Drawing Sheets

TRACHEOTOMY PROCEDURE WITH INTEGRATED TOOL

FIELD OF THE INVENTION

The present invention relates generally to surgical procedures, and more particularly to tracheotomy procedures utilizing an integrated tool.

BACKGROUND

A tracheotomy is a surgical procedure in which a cut or opening is made in the trachea. The term tracheostomy is sometimes used interchangeably with tracheotomy, although the word "tracheostomy" generally refers to the opening itself while the word "tracheotomy" generally refers to the actual operation. A tube, cannula, stoma stent or other device may be inserted into the tracheostomy to hold it open, bypass an obstruction and/or allow air to get to the lungs.

Typically, an emergency tracheotomy is performed only as a last-resort procedure, when the patient's trachea is obstructed and the situation is life-threatening. Such an emergency situation may occur, for example, where the trachea is blocked by swelling that results from anaphylactic shock, or from a severe trauma to the neck, nose or mouth, or where the trachea is blocked by the presence of a foreign object in the larynx. A cut is made with a scalpel or any available tool in a thin part of the larynx called the cricothyroid membrane. An endotracheal tube is then inserted through the cut in the cricothyroid membrane, through which the patient can breathe. As popularized on television and in the movies, in dire situations where no other tools are available, a ballpoint pen casing with the ink cartridge removed may be used to penetrate the cricothyroid membrane or other portion of the trachea, and is then left in place to allow the patient to breathe through it. An emergency tracheotomy also is called a cricothyroidotomy. In this document, the terms "tracheotomy" and "cricothyroidotomy" are used synonymously and interchangeably.

Emergency tracheotomies or cricothyroidotomies are generally disfavored, in part due to the potential for error. The person performing the procedure may have minimal or no medical training, and as a result may cause more injury attempting the procedure than would have resulted without it. One potential for error lies in the proper placement of the endotracheal tube, which should be at the cricothyroid membrane and not through the cartilage of the trachea. Another potential for error lies in the inadvertent puncture of the opposite wall of the trachea during performance of the tracheotomy. In addition, placement of a tube, cannula, stoma stent, or similar device in the resultant tracheostomy to prevent it from closing may be difficult, particularly if the person performing the procedure has minimal or no medical training.

Referring to FIG. 1, the trachea 2 of a patient includes a number of tracheal cartilage rings 4. Adjacent tracheal cartilage rings 4 are spaced apart from one another and connected by membranes 6. The larynx 8 is located at the superior end of the trachea 2. The thyroid cartilage 10 is positioned adjacent to and anterior to part of the larynx 8. The thyroid cartilage 10 is usually prominent in males, where a portion of it protrudes as the Adam's apple. The cricoid cartilage 12 is located superior to the uppermost tracheal cartilage ring 4, spaced apart from that ring 4 and connected to it by a membrane 6. An indentation 14 is present on the anterior surface of the cricoid cartilage 12, inferior to the thyroid cartilage 10. The cricothyroid membrane 16 is positioned in that indentation 14. Although different patients may exhibit variations, the anatomy shown in FIG. 1 is standard.

BRIEF DESCRIPTION OF THE DRAWINGS

The use of the same reference symbols in different figures indicates similar or identical items.

DETAILED DESCRIPTION

Integrated Tracheotomy Tool

Figure 2:
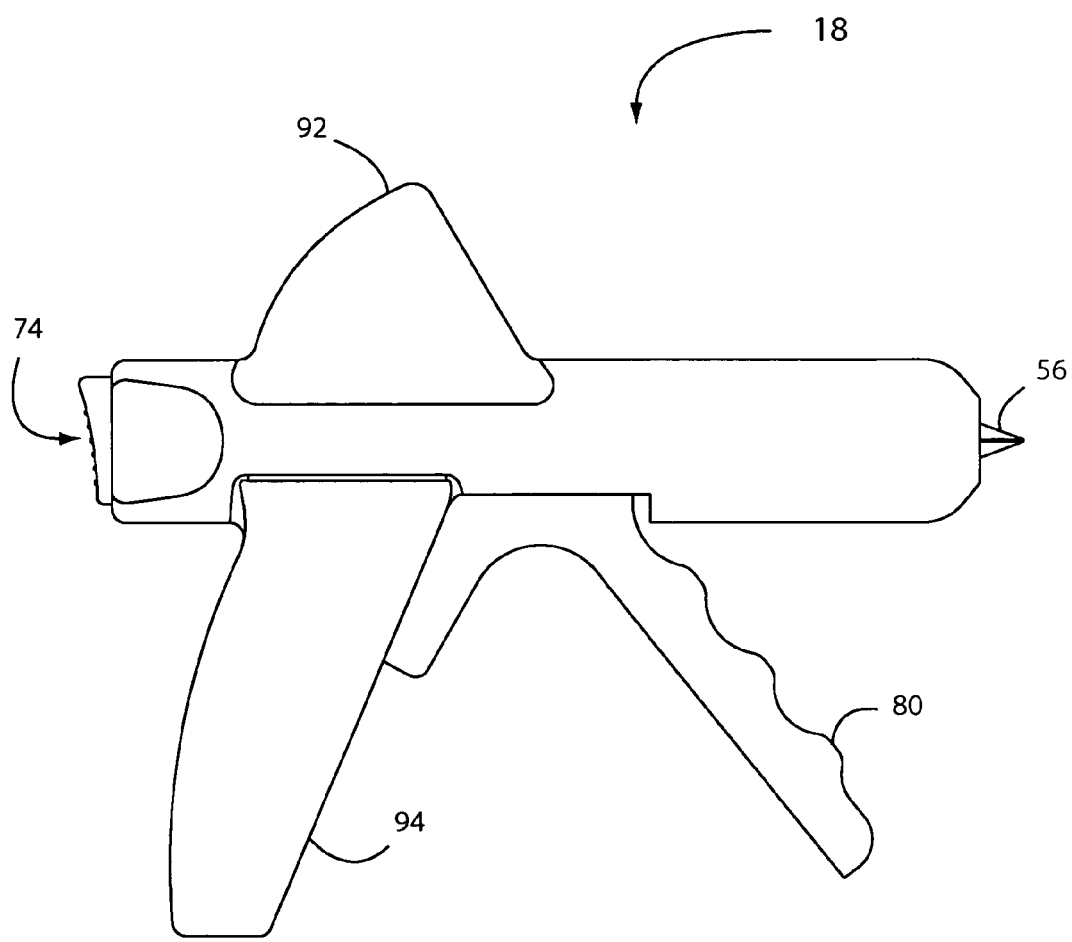
FIG. 2 is a side view of an integrated tracheotomy tool in a first position.
Figure 3:
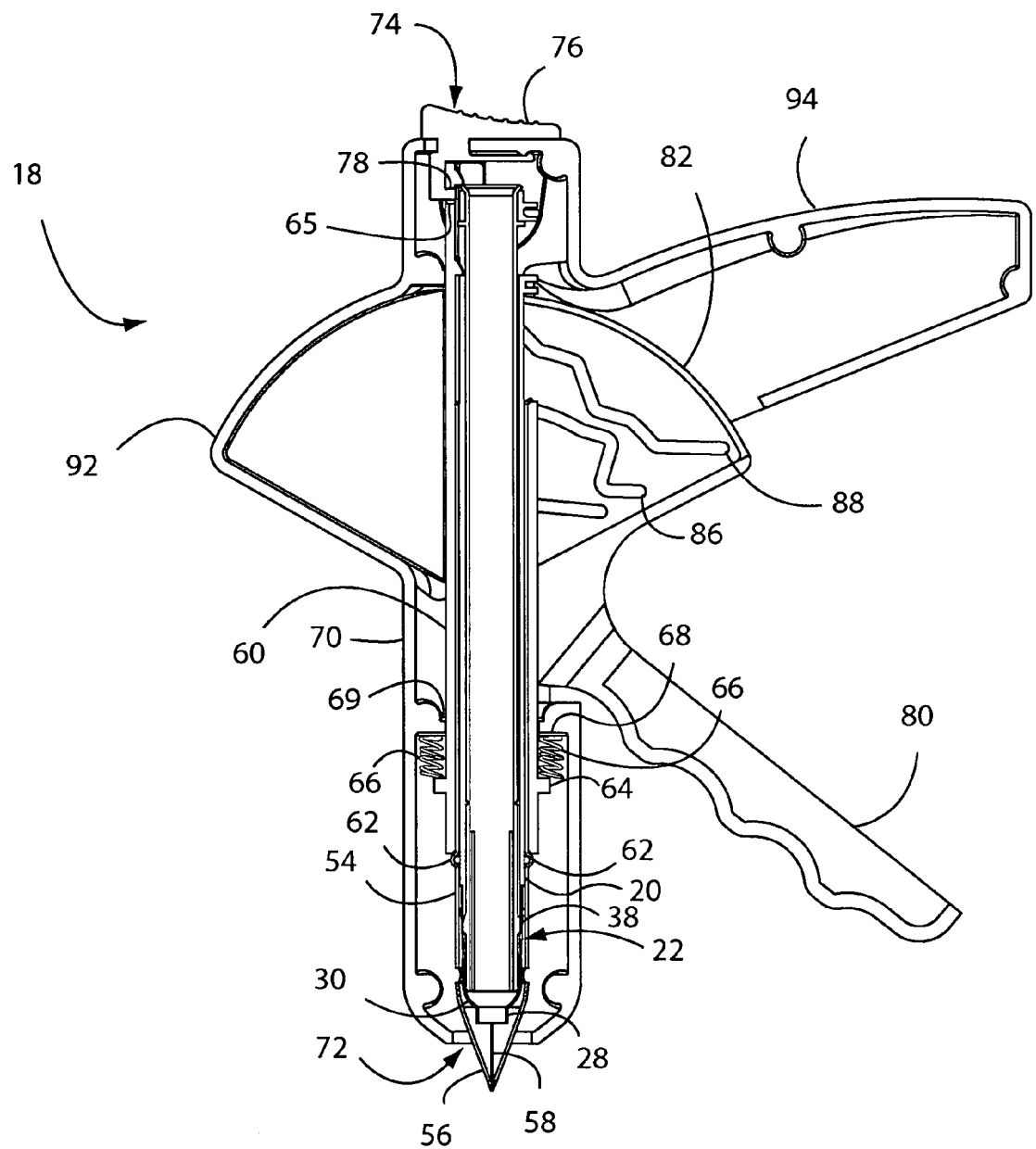
FIG. 3 is a side cross-section view of the integrated tracheotomy tool of FIG. 1 in an initial configuration.

Referring to FIGS. 2-3, an exemplary integrated tool 18 used to perform a tracheotomy is shown, in an initial configuration. As used in this document, the term "tracheotomy" includes any procedure in which an opening is created in any portion of the trachea, such as tracheotomy, cricoidectomy, cricothyrotomy and cricotracheotomy. The integrated tool 18 may include a crown 20 that holds a stoma stent 22 at or near its distal end. The crown 20 may be a tube. Advantageously, the crown 20 is configured in a manner similar to the crown disclosed in commonly-owned U.S. Pat. No. 6,962,595 to Chamness et. al., which is hereby incorporated by reference in its entirety. Alternately, the crown 20 may be configured in any other suitable manner. The crown 20 includes at least one crown cam follower (not shown) extending therefrom. Each crown cam follower may be a pin, stud or any other suitable structure or mechanism. Each crown cam follower may be positioned at any suitable location along the length of the crown 20.

Figure 4:
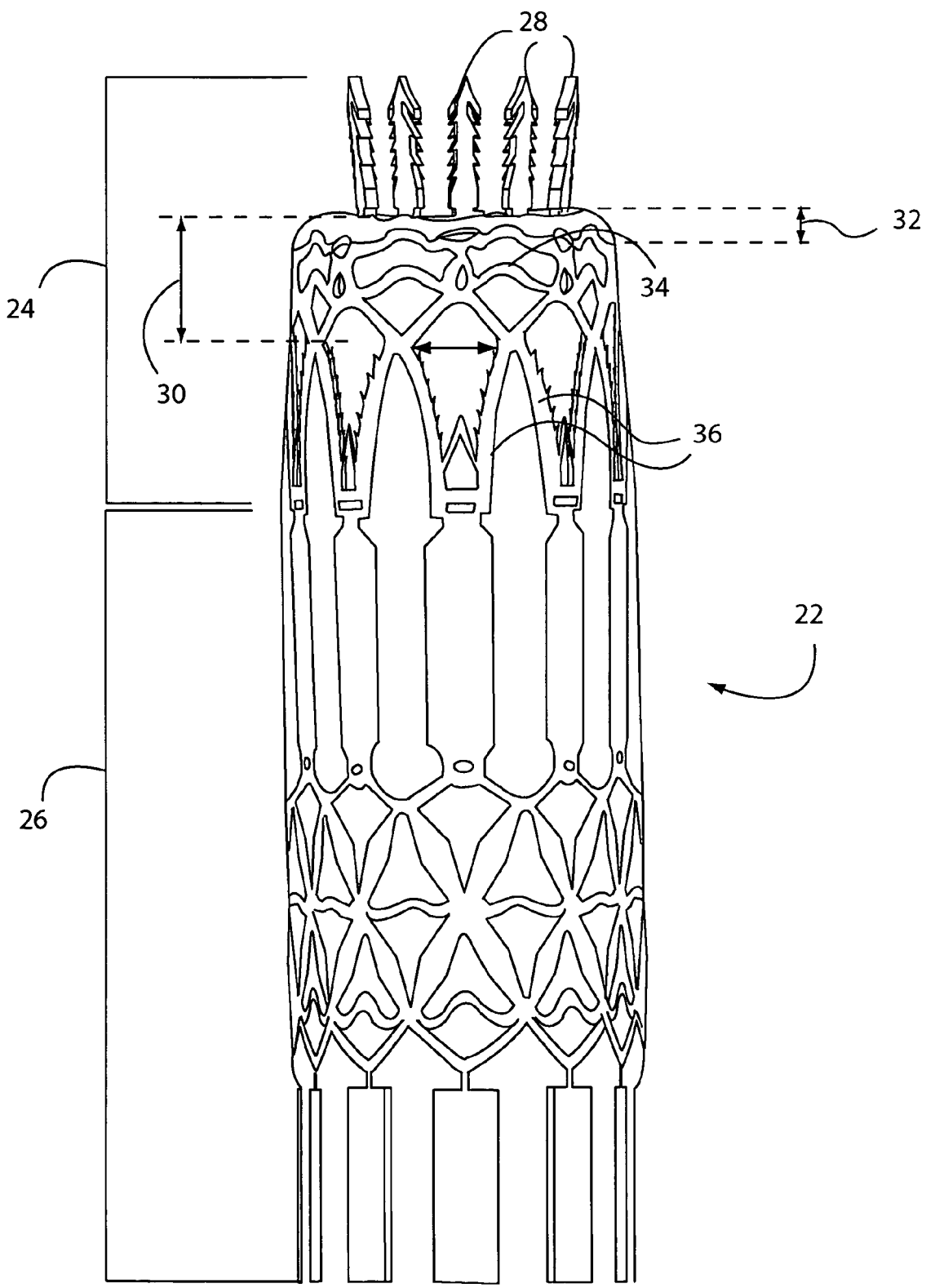
FIG. 4 is a side view of a stoma stent used in the integrated tracheotomy tool of FIG. 1, in an initial configuration.

Referring also to FIG. 4, advantageously an exemplary stoma stent 22 is configured in a manner analogous to the configuration of the anastomosis device disclosed in U.S. Pat. No. 6,962,595. Advantageously, the stoma stent 22 may be fabricated to have a larger diameter, width and/or thickness than the anastomosis device disclosed in U.S. Pat. No. 6,962,595. The stoma stent 22 may be connected to the crown 20 in any suitable manner. For example, the stoma stent 22 may include a deployable section 24 and a discard section 26 that are frangibly connected to one another. The discard section 26 may be fixed to the crown 20, such as by welding, adhesive, mechanical connection, or in any other suitable manner. The deployable section 24 may include a plurality of inner flange tines 28 at its distal end. The inner flange tines 28 may be oriented generally longitudinally before the stoma stent 22 is deployed, or may be oriented in any other suitable direction. The proximal end of each inner flange tine 28 may be connected to a linkage 30 that is configured to form the body of the deployable section 24. The linkage 30 may curve or otherwise protrude inward at its distal end, and that inward-curving or -protruding section of the linkage 30 may be referred to as the ring 32. The ring 32 and/or a remainder of the linkage 30 may be configured to expand radially during deployment, as is described in greater detail below. Thus, the linkage 30 may include a number of generally circumferentially-positioned expandable members 34, such that the linkage 30 is free to expand radially upon the application of an appropriate force. A plurality of outer flange arms 36 may be connected to and extend generally proximally from the linkage 30. The outer flange arms 36, like the inner flange tines 28 and the linkage 30, may be configured in any suitable manner. As one example, at least one outer flange arm 36 may be generally V-shaped, with the open end of the V-shape connected to the linkage 30. The proximal end of each outer flange arm 36 may be frangibly connected to the distal end of the discard section 26. Optionally, at least the linkage 30 of the stoma stent 22 may be covered with DACRON® brand polyester fiber, PTFE, or any other suitable biocompatible covering or coating. Further, the stoma stent 22 optionally may be coated at least in part with collagen and/or a different substance or substances to minimize bleeding, promote healing or perform any other suitable therapeutic purpose.

At least part of an expander 38 is positioned within the crown 20. The expander 38 may be generally tubular, and may be substantially coaxial with the crown 20. The expander 38 may be slidable relative to the crown 20. Advantageously, the expander 38 is configured in a manner similar to the expander disclosed in U.S. Pat. No. 6,962,595. The expander 38 includes at least one expander cam follower (not shown) extending therefrom. Each expander cam follower may be a pin, stud, or any other suitable structure or mechanism. Each expander cam follower may be positioned at any suitable location along the length of the expander 38.

Figure 5:
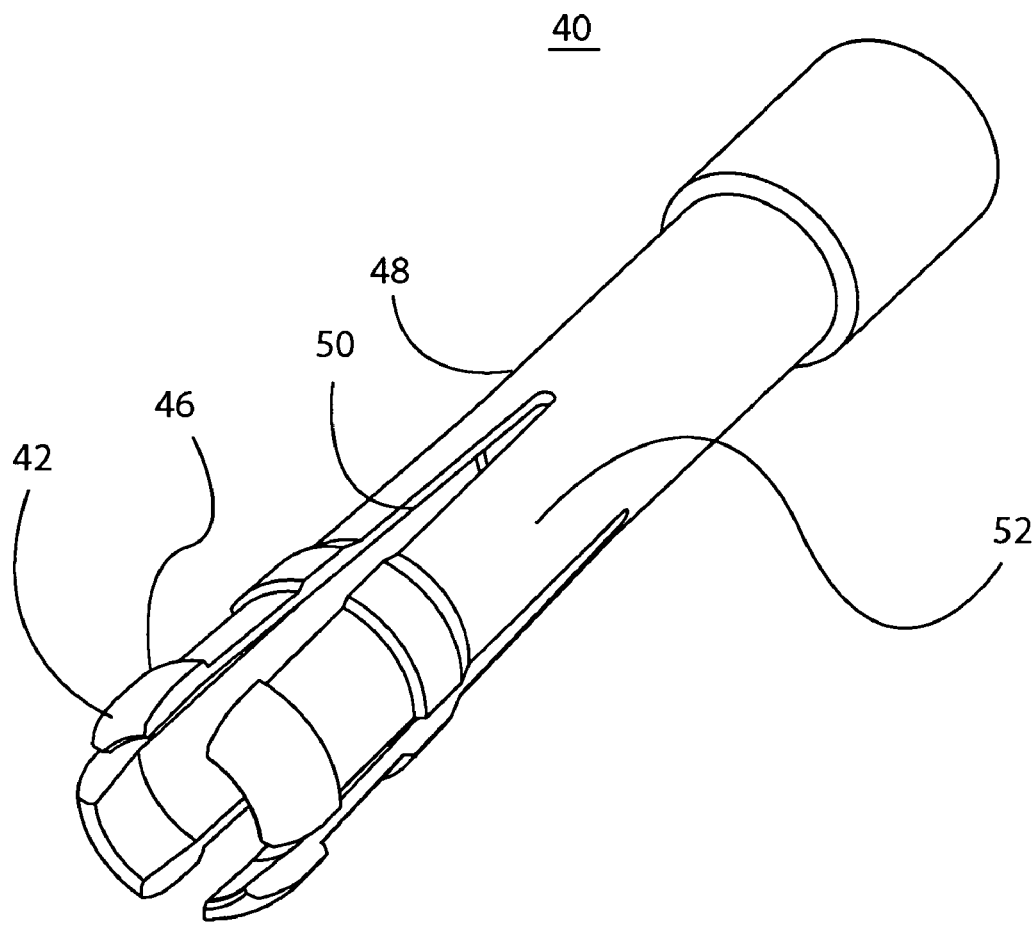
FIG. 5 is a perspective view of an expander tip used in the integrated tracheotomy tool of FIG. 1.

Referring also to FIG. 5, the distal end of the expander 38 may be referred to as the expander tip 40. The expander tip 40 may include an expander head 42 at or near its distal end. The expander head 42 may have a diameter larger than the diameter of the portion of the expander tip 40 immediately proximal to the expander head 42 The expander head 42 may extend substantially circumferentially around the expander tip 40. The expander head 42 may include a shoulder 46 at its proximal end, which forms any suitable angle with the surface of the body 48 of the expander tip 40. The expander tip 40 may have a lumen therethrough and one or more slots 50 defined therein. The slots 50 may extend substantially longitudinally from the distal end of the expander tip 40 through the expander head 42. The segments 52 of the expander tip 40 between the slots 50 each may be biased outward relative to the axis of the expander tip 40. If so, the expander head 42 may have a larger outer diameter than the inner diameter of the ring 32 of the stoma stent 22 when one or more segments 52 are at least partially free to move outward as a result of that outward bias. Alternately, the segments 52 are not biased outward relative to the axis of the expander tip 40. The slots 50 may be spaced evenly, or unevenly, around the circumference of the expander tip 40. Any suitable number of slots 50 and segments 52 may be provided. A sleeve (not shown) may be positioned around at least part of the expander tip 40, such as disclosed in U.S. Pat. No. 6,962,595.

A trocar 54 is positioned outside the crown 20. At least a portion of the trocar 54 is tubular, and is configured to receive at least a portion of the crown 20 therein. The trocar 54 and the crown 20 may be substantially coaxial. Advantageously, the trocar 54, expander 38 and crown 20 are substantially coaxial with one another. The trocar 54, expander 38 and crown 20 are arranged in a manner similar to that disclosed in commonly-owned U.S. Pat. No. 6,428,550, which is hereby incorporated by reference in its entirety. The trocar 54 may have a pointed tip 56, which may be substantially conical, or may be shaped in any other suitable manner. The tip 56 of the trocar 54 may have a plurality of slots 58 defined therein that extend proximally from the distal end of the tip 56 of the trocar 54, oriented substantially longitudinally or in any other manner. Consequently, segments of the tip 56 of the trocar 54 may be spread apart from one another as a result of contact with the stoma stent 22, crown 20 and/or expander 38 during distal motion of the crown 20 and/or expander 38. Initially, at least part of the tip 56 of the trocar 54 may be positioned outside the housing 70 of the integrated tool 18, extending through an aperture 72 or other opening in the distal end of the housing 70. Alternately, the tip 56 of the trocar 54 may be positioned differently when the integrated tool 18 is in the initial position; for example, the tip 56 of the trocar 54 may be located entirely within the housing 70. The trocar 54 includes at least one trocar cam follower (not shown) extending therefrom. Each trocar cam follower may be a pin, stud or any other suitable structure or mechanism. Each trocar cam follower may be positioned at any suitable location along the length of the trocar 54.

A trocar driver 60 may be positioned around at least part of the trocar 54. The trocar driver 60 may be substantially tubular, and may be substantially coaxial with the trocar 54. The trocar driver 60 may be slidable or otherwise movable relative to the trocar 54. The distal end of the trocar driver 60 may be configured to engage a ridge 62 on the surface of the trocar 54. The ridge 62 may extend circumferentially around the trocar 54. Alternately, the ridge 62 may be one or more bumps or other raised areas on the trocar 54. The ridge 62 extends outward from the surface of the trocar 54 sufficiently far to prevent the distal end of the trocar driver 60 from moving distal to that ridge 62. That is, as the trocar driver 60 slides distally, the distal end of the trocar driver 60 engages the ridge 62 rather than passing over it. Alternately, the trocar driver 60 may be fixed to the trocar 54 in any suitable manner. Alternately, the trocar driver 60 may be omitted, and one or more features of the trocar driver 60 may be integrated into the trocar 54 itself.

A flange 64 extends outward from the surface of the trocar driver 60 at a location spaced apart from the distal end of the trocar driver 60. Alternately, the flange 64 may be positioned substantially at any other location on the trocar driver 60. The flange 64 may extend circumferentially around the trocar driver 60. Alternately, the flange 64 may be interrupted by one or more spaces, such that the flange 64 includes multiple segments extending from the trocar driver 60. The trocar driver 60 may include a slot 65 defined therein to receive a tab of a safety switch, which is described in greater detail below. Alternately, the trocar driver 60 may be omitted, and the flange 64 may extend from the trocar 54 itself.

At least one spring 66 may be located between the flange 64 and an inner wall 68 of the housing 70 of the integrated tool 18. The flange 64 extends far enough outward from the wall of the trocar driver 60 to engage the spring or springs 66 and substantially prevent the spring or springs 66 from moving distal to the flange 64. Advantageously, the spring or springs 66 are compression springs. Alternately, at least one spring 66 may be of a different type. Alternately, at least one spring 66 may be an extension spring. The integrated tool 18 includes a housing 70 that is at least partially hollow in order to receive at least part of the crown 20, expander 38, trocar 54, trocar driver 60, spring or springs 66, and/or other components therein. The inner wall 68 of the housing 70 may be oriented substantially perpendicular to the longitudinal axis of the trocar driver 60, or may be oriented in any other suitable manner. The inner wall 68 includes at least one aperture 69 therethrough to allow one or more components that are present in the housing to extend through the inner wall 68. The inner wall 68 engages the proximal end, or any other suitable portion, of the spring or springs 66. Alternately, the proximal end of the spring or springs 66 engages or is connected to a structure or mechanism other than the inner wall 68 of the housing 70. If so, the inner wall 68 of the housing 70 may be omitted, and one or more stubs, tabs or other structures may be utilized instead. In the initial configuration of the integrated tool 18 shown in FIG. 3, the spring or springs 66 store energy. For example, where the spring or springs 66 are compression springs, the spring or springs 66 are held in compression between the flange 64 and the inner wall 68 of the housing 70 when the integrated tool 18 is in the initial configuration.

Optionally, the integrated tool 18 may include a safety switch 74. The safety switch 74 may be positioned at the proximal end of the integrated tool 18, or at any other suitable location on the integrated tool 18. The safety switch 74 may include an input feature 76 outside the housing 70 of the integrated tool 18, placed and configured to be actuated by the user. The safety switch 74 may include a tab 78 or other structure connected to the input feature 76. The tab 78 is positioned such that it can engage the slot 65 of the trocar driver 60 when the integrated tool 18 is in the initial configuration. When the tab 78 engages the slot 65 of the trocar driver 60, the tab 78 substantially restrains the trocar 54 against distal motion, thereby preventing inadvertent deployment of the trocar 54.

Figure 6:
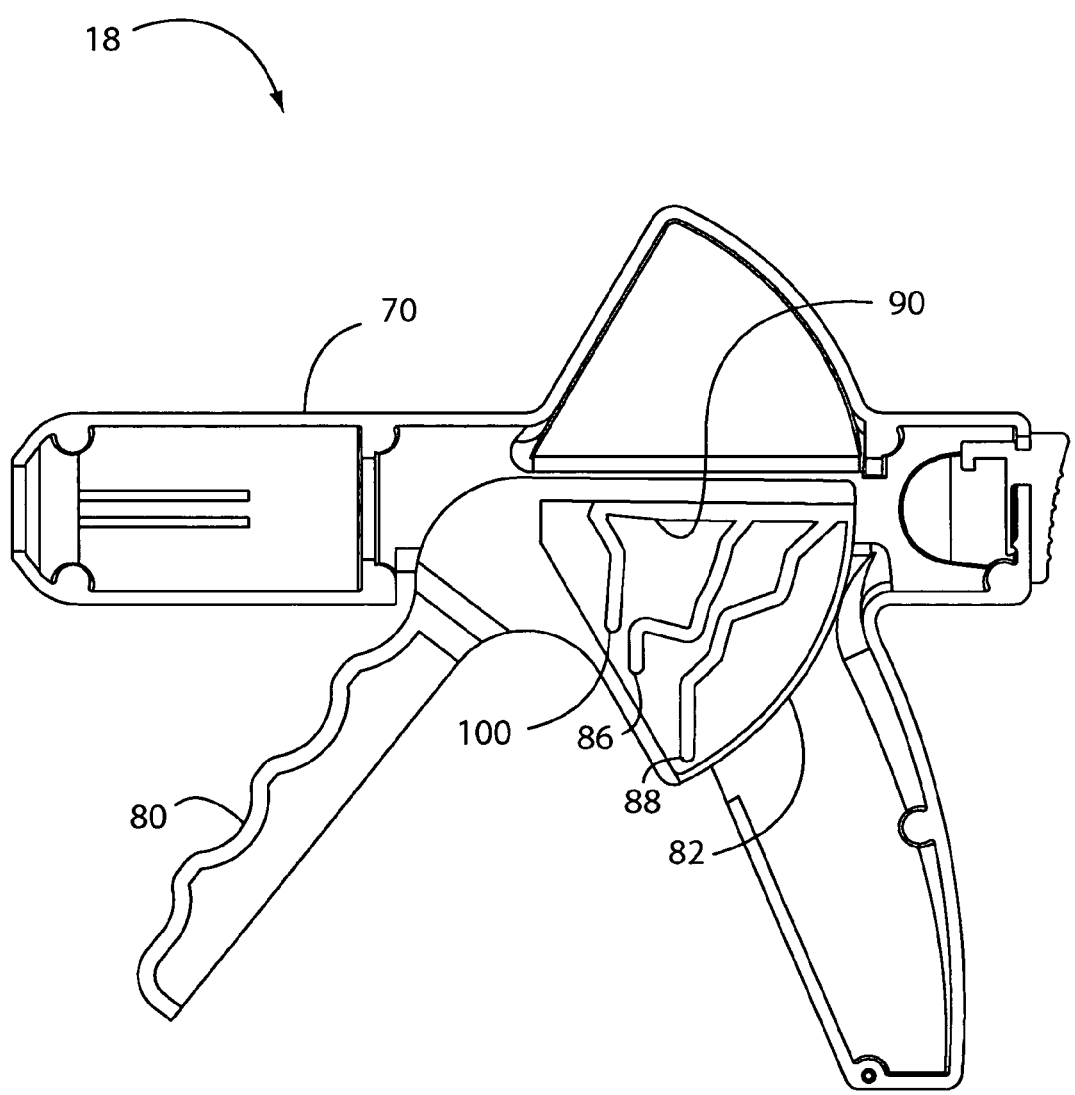
FIG. 6 is a side view of a cam plate and trigger of the integrated tracheotomy tool in the initial configuration relative to the housing of the integrated tracheotomy tool.

The integrated tool 18 may include a control such as a trigger 80. Referring also to FIG. 6, the trigger 80 is connected to at least one cam plate 82. Advantageously, two cam plates 82 are provided, spaced apart from one another laterally. Advantageously, the trigger 80 and cam plate or plates 82 are fabricated as a single piece. The trigger 80 and cam plate or plates 82 may rotate as a unit about a pivot point 84 that may be any structure or mechanism that allows the trigger 80 and cam plate 82 to pivot relative to the housing 70. For example, the pivot point 84 may be an aperture in the trigger 80 or cam plate or plates 82 configured to receive a post (not shown) in or connected to the housing 70 of the integrated tool 18. As another example, the pivot point 84 may be a post or rod that is configured to engage one or more apertures or depressions (not shown) in the housing 70 of the integrated tool 18. Alternately, the trigger 80 and the cam plate 82 may move linearly in addition to, or instead or, moving rotationally.

Each cam plate 82 includes one or more cam paths defined therein. Each cam path is configured in any suitable manner to engage a corresponding cam follower as described above. As one example, a cam path in the cam plate 82 may be a slot through or a trough in that cam plate 82 that engages a corresponding cam follower that is configured as a pin. Any suitable number of cam paths may be provided in a cam plate 82. As one example, each cam plate 82 may include a crown cam path 86 configured to engage the crown cam follower, an expander cam path 88 configured to engage the expander cam follower, and a trocar cam path 100 configured to engage the trocar cam follower. Each cam plate 82 also may include a first path 90 that intersects an end of each of the other cam paths 86, 88, 100. The first path 90 is configured to be substantially parallel to the longitudinal centerline of the crown 20 when the integrated tool 18 is in its initial configuration. In this way, the cam followers are able to slide distally when the trocar 54 is deployed, as described in greater detail below.

The housing 70 may include a cam plate cover 92 that prevents external interference with the cam plate or plates 82 during their motion. The housing 70 may include a handle 94, such that the user can place the handle 94 in his or her palm and actuate the trigger 80 with his or her fingers.

Operation

Figure 1:
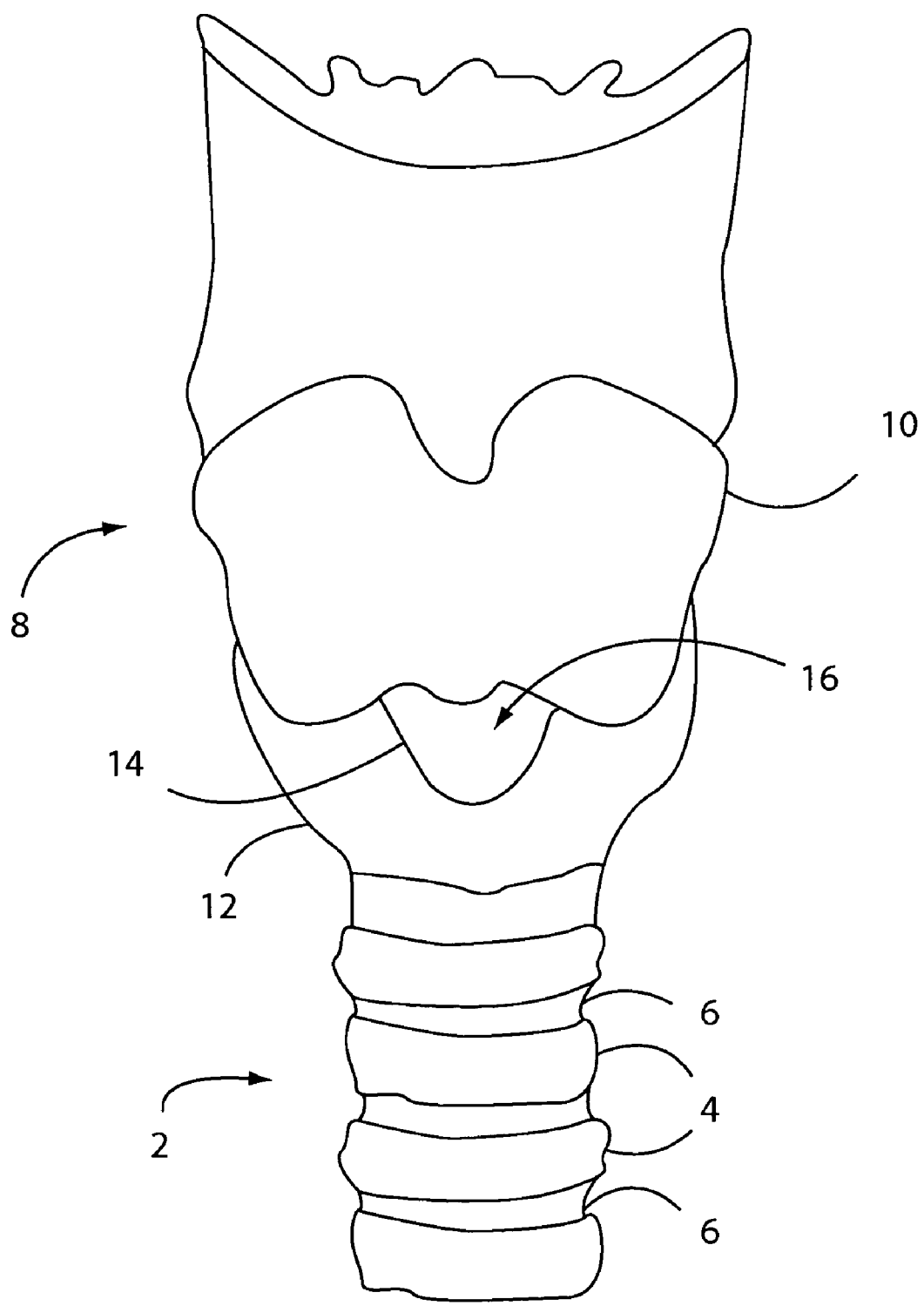
FIG. 1 is a front view of the tracheal anatomy.

To perform a tracheotomy, the patient is placed on his or her back. Advantageously, an object is placed under the patient's neck, and the patient's head is hyperextended. That is, referring also to FIG. 1, the patient's chin is rotated away from his or her chest, exposing the neck and causing the trachea 2 to move closer to the skin. Next, the site of the tracheotomy is located. The tracheotomy may be performed at the cricothyroid membrane 16. If so, the cricothyroid membrane 16 may be found by touch: the person performing the procedure feels the skin of the patient and probes with a finger for the indentation 14 in the cricoid cartilage 12. The cricothyroid membrane 16 is located in that indentation 14 between the thyroid cartilage 10 and the cricoid cartilage 12. Particularly in male patients, it may be advantageous to locate the Adam's apple by touch, and move slightly inferior to that in order to find the indentation 14.

Referring also to FIG. 4, the tip of the trocar 54 of the exemplary integrated tool 18 initially may extend out of the distal end of the housing 70 of that integrated tool 18. The configuration of the integrated tool 18 prior to its use, as shown in FIG. 3, is referred to as the initial configuration. When the tip 56 of the trocar 54 is placed against the tracheotomy site and urged distally, the tip 56 of the trocar 54 penetrates the skin of the patient, and may penetrate at least partially the cricothyroid membrane 16, a membrane between adjacent tracheal cartilage rings 4, and/or a tracheal cartilage ring itself, depending on the selected tracheotomy site. The distance to which the tip 56 of the trocar 54 penetrates the skin of the patient is limited by contact between the patient's body and the distal end of the housing 70 of the integrated tool 18. In this way, the trocar 54 acts as a probe to determine whether the distal end of the integrated tool 18 has been properly positioned at the intended tracheotomy site. For example, where the cricothyroid membrane 16 has been selected as the tracheotomy site, the tip 56 of the trocar 54 should easily pass into the cricothyroid membrane 16; if the tip 56 of the trocar 54 encounters hard tissue, then the distal end of the integrated tool 18 has been positioned at a location other than the intended tracheotomy site. Thus, the tip 56 of the trocar 54 may be used in probing a potential tracheotomy site. In this way, locating the tracheotomy site thus may be performed simultaneously with placing the integrated tool 18 at the tracheotomy site. Alternately, a separate probe may be used to locate the tracheotomy site. Alternately, the tracheotomy may be performed between adjacent tracheal cartilage rings 4 at a location other than the cricothyroid membrane. If so, the adjacent tracheal cartilage rings 4 are found by touch, and the space between those adjacent tracheal cartilage rings 4 is apparent. Alternately, the tracheotomy may be performed directly through at least part of one or more tracheal cartilage rings 4, which may be necessary or unavoidable in an emergency situation. Alternately, the tracheotomy may be performed as an over-the-wire technique, where a needle is used to determine the ideal location and is inserted at the tracheotomy site. A wire may be advanced through the needle, after which the needle is removed. The integrated tool 18 then may be advanced over-the-wire to the tracheotomy site.

Next, the integrated tool 18 is actuated to create an opening at the intended tracheotomy site. For clarity, the intended tracheotomy site will be described here and below as the cricothyroid membrane 16, although this does not limit the possible tracheotomy sites to the cricothyroid membrane 16. The safety switch 74, if utilized in the integrated tool 18, is actuated to remove the tab 78 of the safety switch 74 from the slot 65 of the trocar driver 60, or to perform any other action that frees the trocar driver 60 to move distally.

The trocar 54 is then fired through the cricothyroid membrane 16, creating an opening therein. The trocar 54 may be fired by pulling the trigger 80 toward the handle 94, such that actuation of the safety switch 74 alone does not cause the trocar 54 to fire. For example, a pin or other lockout (not shown) on at least one cam plate 82 may be positioned to engage and hold the trocar driver 60 until the trigger 80 is pulled a small amount to move that pin or lockout out of engagement with the trocar driver 60 and allow it to move distally. Actuation of the trigger 80 frees the trocar driver 60, and the energy stored in the spring or springs 66 causes the spring or springs 66 to move longitudinally. The movement of the spring or springs 66 against the flange 64 of the trocar driver 60 causes the freed trocar driver 60 to move distally. The distal end of the trocar driver 60 in turn contacts and pushes against the ridge 62 of the trocar 54, causing the trocar 54 to move distally. Alternately, if the trocar drive 60 is not utilized, the movement of the spring or springs 66 may move the trocar 54 in the distal direction by direct engagement. The spring or springs 66 release enough energy during their expansion to urge the trocar 54 distally to penetrate the cricothyroid membrane 16 or other anticipated tracheotomy site. Advantageously, the trocar 54 is urged in the distal direction as a result of an impulsive force applied to it by the spring or springs 66 or other energy storage mechanism; an "impulsive force" is a force that acts on a body for a short time but produces a large change in its linear or angular momentum. As the trocar 54 moves distally, each trocar cam follower moves along the first path 90 in the corresponding cam plate 82. Alternately, the trocar 54 may fire automatically when the safety switch 74 is actuated to free the trocar driver 60, without the need for an input to the trigger 80. Alternately, any energy storage device may be used in addition to or in conjunction with the spring or springs 66. As one example, one or more balloons (not shown) may be utilized instead of or in conjunction with the spring or springs 66, connected to a cartridge of carbon dioxide or other gas. Upon actuation of the safety switch, or after the trigger is pulled a small amount, that gas may rush into the balloon or balloons to push the flange 64 of the trocar driver 60 and thereby move the trocar 54 distally. As another example, a moveable piston (not shown) within a cylinder (not shown) may be used, where the piston is operatively coupled to the trocar 54. Upon actuation of the safety switch, or after the trigger is pulled a small amount, that gas may rush into the cylinder to push the piston and thereby move the trocar 54 distally.

The integrated tool 18 is configured to move the trocar 54 distally a fixed amount that is less than the inside diameter of the trachea 2. In this way, the tip 56 of the trocar 54 does not encounter or penetrate the opposite side of the trachea 2 after piercing the cricothyroid membrane 16. The distance that the trocar 54 travels distally during firing may be controlled in any suitable manner. As one example, the trocar driver 60 includes a cam follower that engages the trocar cam path 100 defined in at least one cam plate 82, and the interaction between the cam follower and the trocar cam path 100 restricts the distal motion of the trocar driver 60 and thus the trocar 54 during firing. As another example, the flange 64 of the trocar driver 60 may contact the inner surface of the housing 70 adjacent to the aperture 72 in the distal end of the housing 70. Such contact stops the distal motion of the trocar driver 60 and thus the trocar 54. Optionally, the trocar 54 may be a safety trocar. Safety trocars are standard in the art, and as one example may be configured in a manner similar to that disclosed in U.S. Pat. No. 5,690,663, which is hereby incorporated by reference in its entirety. The tip 56 of the trocar 54 may be shielded or otherwise rendered safe after the initial penetration of the trachea 2. Thus, the trocar 54 can travel along a fixed distance during firing without the tip 56 puncturing the rear wall of the trachea 2 in the event that motion of the trocar 54 along that fixed distance causes the tip 56 to encounter that rear wall. As a result, the integrated tool 18 that includes a safety trocar may be used across a spectrum of patients having different depths of tissue between the surface of the skin and the inner surface of the trachea 2. Alternately, the distance that the trocar 54 travels distally during firing may be adjusted by the user.

After its firing, the trocar 54 is positioned across the cricothyroid membrane 16. Also at this time, the crown 20 and the expander 38 have advanced distally with the trocar 54. Such advancement may be performed in any suitable manner. As one example, the crown 20, expander 38 and trocar 54 are fit together closely enough that frictional force between the crown 20 and the trocar 54 moves the crown 20 distally as the trocar 54 is urged distally by the spring or springs 66, and in turn frictional force between the expander 38 and the crown 20 moves the expander 38 distally at the same time. As the crown 20 and the expander 38 move distally, their cam followers move along the first path 90 in each cam plate 82 as described above, which may be aligned substantially parallel to the longitudinal centerline of the trocar 54. Alternately, the crown 20 and the expander 38 may remain in place as the trocar 54 moves distally. Alternately, at least one of the cam followers moves along a cam path separate from the first path 90.

The user then pulls, or continues to pull, the trigger 80 toward the handle 94. At this time, the crown cam follower is located adjacent to one end of the crown cam path 86, the expander cam follower is located adjacent to one end of the expander cam path 88, and the trocar cam follower is located adjacent to one end of the trocar cam path 100. Continued motion of the trigger 80 engages the crown cam path 86 with the crown cam follower, engages the expander cam path 88 with the expander cam follower, and engages the trocar cam path 100 with the trocar cam follower. Alternately, at least one cam follower is already in position within the corresponding cam path 86, 88, 100.

As the user continues to pull the trigger 80 toward the handle 94, engagement between the crown cam follower and the corresponding crown cam path 86 and between the expander cam follower and the corresponding expander cam path 88 advances the crown 20 and the expander 38 distally along the interior of the trocar 54. The crown 20 and expander 38 may be referred to collectively as the delivery mechanism. As the crown 20 moves distally, a portion of the crown 20 in proximity to its distal end and/or the stoma stent contacts the inner surface of the tip 56 of the trocar 54. This contact causes the tip 56 of the trocar 54 to split. That is, segments between the slots 58 of the tip 56 move outward away from the longitudinal centerline of the trocar 54 as a result of the force exerted on the tip 56 by the crown 20 and/or the stoma stent 22. As the tip 56 of the trocar 54 splits, it increases in diameter. If the tip 56 is located in the cricothyroid membrane 16, then the increase in its diameter enlarges the opening in the cricothyroid membrane 16.

Next, the integrated tool 18 is actuated to deploy the stoma stent 22 in the tracheotomy. Advantageously, a single control such as the trigger 80 is used both to create the tracheotomy and to deploy the stoma stent, such that both actions are accomplished with a single input to the single control. The crown 20 and the expander 38 translate substantially together into the tracheostomy. Alternately, the crown 20 and expander 38 move in a different manner into the tracheostomy. The stoma stent 22 is then deployed. Such deployment may be performed in any suitable manner. Advantageously, deployment is performed in a manner analogous to the anastomosis device deployment set forth in U.S. Pat. No. 6,962,595. The crown 20 is held substantially in place, thereby holding the stoma stent 22 substantially in place, as the expander 38 is translated distally. As the expander 38 moves distally, it engages the ring 32 of the stoma stent 22 and applies a force to it. This force causes the stoma stent 22 to deform, deflecting a plurality of inner flange tines 28 of the stoma stent 22 outward away from the longitudinal centerline of the stoma stent 22 and forming an inner flange 96. The ring 32 may expand radially as well as a result of lateral force exerted against it as the expander head 42 moves distally into and/or through the ring 32. The crown 20, expander 38 and trocar 54 are then moved proximally together until the inner flange 96 seats against the inner surface of the cricothyroid membrane 16. This proximal motion may be caused and controlled by motion of the cam plate 82. One or more of the inner flange tines 28 may penetrate the tissue of the cricothyroid membrane 16 to better hold the stoma stent 22 in place. Alternately, the trocar 54 is moved proximally prior to deployment of the inner flange. If so, the inner flange 96 may be deployed directly onto the inner surface of the cricothyroid membrane 16, such that the crown 20 and expander 38 need not be translated proximally after deployment of the inner flange 96.

Next, the trocar 54 is moved proximally out of the opening of the cricothyroid membrane 16, if it has not been moved out of the opening in the cricothyroid membrane 16 during deployment and/or seating of the inner flange 96 of the stoma stent 22. The expander 38 is then held in place and the crown 20 is advanced. Advancement of the crown 20 pushes the stoma stent 22 against the shoulder 46 of the expander head 42, thereby applying a compressive force to the undeployed portion of the stoma stent 22. This compressive force causes a plurality of outer flange arms 36 to deflect outward away from the longitudinal centerline of the stoma stent 22 and form an outer flange 98. The stoma stent 22 may be configured in any suitable manner to cause such deflection of the outer flange arms 36. As one example, referring to U.S. Pat. No. 6,962,595, the intersection of each outer flange arm 36 and the discard section 26 may be further from the longitudinal centerline of the stoma stent 22 than both the distal end of each outer flange arm 36 and a portion of the discard section 26 proximal to and spaced apart from the distal end of the discard section 26. As a result, an outward moment is produced on the stoma stent 22 at the intersection of each outer flange arm 36 and the discard section 26 as a result of the axial compressive stress exerted on the stoma stent 22. That outward moment deploys the outer flange arms 36, and also causes buckling at the intersections between the outer flange arms 36 and the discard section 26, releasing the deployable section 24 from the discard section 26. Alternately, the outer flange arms 36 are deployed in a different manner. Alternately, the discard section 26 is omitted, and the entire stoma stent 22 is deployed into the patient without separation of any part of the stoma stent 22 from any remaining part of itself. The outer flange 98 is deployed onto the skin of the patient. One or more of the outer flange tines 98 may penetrate the skin to better hold the stoma stent 22 in place. The deployed stoma stent 22 may compress tissue between the inner flange 96 and the outer flange 98. In this way, the stoma stent 22 may hold itself securely in place in tissue with a thickness throughout a wide range, thereby facilitating its use across a broad spectrum of patients.

Figure 7:
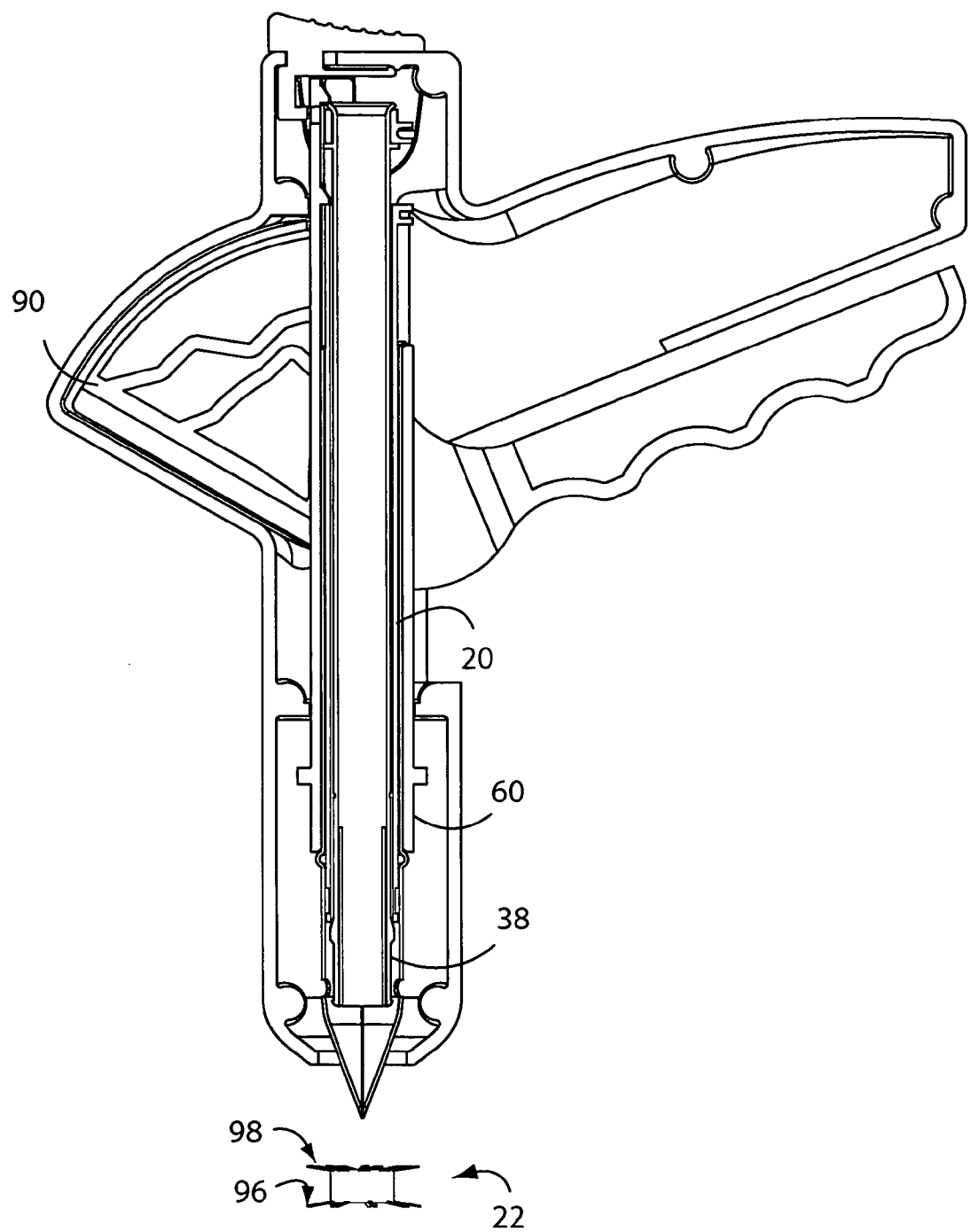
FIG. 7 is a side cross-section view of the integrated tracheotomy tool of FIG. 1 in a final configuration.

The expander 38 is then withdrawn through the center of the stoma stent 22, and the integrated tool 18 is removed from the patient. The integrated tool 18 is now in the final configuration, as shown in FIG. 7.

At this point, the stoma stent 22 has been deployed in the tracheostomy. The deployed stoma stent 22 holds the tracheostomy open. The inner flange tines 28 and outer flange arms 36 hold the stoma stent 22 in place relative to the tracheostomy. Further, tissue positioned between the inner flange tines 28 on the one side and the outer flange arms 36 on the other side is compressed, thereby reducing or eliminating any bleeding at the tracheostomy. The stoma stent 22 may simply be left as is in the patient, without any intubation through the stoma stent 22 into the trachea 2. If desired, an endotracheal tube, cannula or other structure can be inserted through the stoma stent 22 into the trachea 2. The stoma stent 22 protects the tracheostomy and allows for convenient exchange of tubes, cannulas or other structures therethrough, as deemed necessary by a medical care provider. Alternately, a tube, cannula or other structure is fixed or may be fixed to the stoma stent 22.

At a later time, the stoma stent 22 may be removed from the patient, if desired. To do so, a forceps or other instrument is used to deflect the outer flange arms 36 back toward their original position. The forceps or other instrument is then used to pull the stoma stent 22 out of the tracheostomy. As the stoma stent 22 is pulled outward, the inner flange tines 28 deflect back toward their original position, allowing the stoma 22 to be removed. The tracheostomy is then patched and/or closed in a standard manner.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method for performing a tracheotomy on a trachea of a patient, comprising:
   providing an integrated tool including a trocar and a delivery mechanism movable within said trocar;
   storing energy within said integrated tool;
   releasing at least part of said stored energy, wherein said releasing applies an impulsive force in the distal direction to said trocar such that said trocar creates an opening in the trachea; and
   deploying a stoma stent in the opening with said delivery mechanism.

2. The method of claim 1, wherein said delivery mechanism includes a crown configured to hold said stoma stent and an expander movable relative to said crown.

3. The method of claim 1, wherein said integrated tool includes a control; further comprising actuating said control, wherein said creating and said deploying are both performed in response to said actuating.

4. The method of claim 3, wherein said actuating is performed with a single input.

5. The method of claim 1, wherein said creating includes penetrating tissue with the distal end of said trocar and expanding the distal end of said trocar.

6. The method of claim 1, wherein said creating is performed through the cricoid membrane.

7. The method of claim 1, further comprising holding the opening open after said creating and during at least part of said deploying.

8. The method of claim 1, wherein said deploying includes expanding a diameter of at least part of said stoma stent.

9. The method of claim 1, wherein said stoma stent includes a deployable section and a discard section connected to and proximal to said deployable section; and wherein said deploying includes separating said deployable section from said discard section.

10. A method for performing a tracheotomy on a trachea of a patient, comprising:
    providing an integrated tool;
    creating an opening in the trachea with said integrated tool;
    placing a stoma stent in the opening with said integrated tool, said stoma stent including a plurality of inner flange tines and a plurality of outer flange tines; and
    deploying said stoma stent, wherein said deploying includes deploying said inner flange tines to create an inner flange positioned within the trachea and deploying said outer flange tines to create an outer flange positioned outside the trachea wherein said creating and said deploying are performed in response to a single input.

11. The method of claim 10, wherein said integrated tool includes an expander, at least part of which is within said stoma stent; and wherein said deploying includes translating said expander relative to said stoma stent.

12. The method of claim 10, further comprising compressing tissue between said inner flange tines and said outer flange tines.

13. The method of claim 10, wherein said deploying deploys said inner flange tines before said outer flange tines.

14. The method of claim 10, further comprising inserting a tube through said stoma stent into the trachea.

15. A method for performing a tracheotomy on a trachea of a patient, comprising:
    providing a tool including a safety trocar;
    applying an impulsive force to said safety trocar to create an opening in the trachea with said safety trocar; and
    deploying a stoma stent in the opening with said tool;
    wherein said creating and said deploying are performed in response to a single input.

16. The method of claim 15, wherein said tool includes a cam plate, and wherein said creating and said deploying are controlled by said cam plate.

17. The method of claim 1, wherein said integrated tool includes a housing in which at least part of said trocar is received, said housing defining an opening through which said trocar extends distally; and wherein said releasing causes said trocar to move distally through said opening relative to said housing.

* * * * *